(12) United States Patent
Ersoez et al.

(10) Patent No.: US 12,123,844 B2
(45) Date of Patent: Oct. 22, 2024

(54) TRANSISTOR COMPRISING A CERAMIC AND AN IONOGEL

(71) Applicant: Robert Bosch GmbH, Stuttgart (DE)

(72) Inventors: Bora Ersoez, Baar-Ebenhausen (DE); Suresh Palale, Singapore (SG); Tino Fuchs, Tuebingen (DE); Walter Daves, Broadwater Park (GB)

(73) Assignee: ROBERT BOSCH GMBH, Stuttgart (DE)

( * ) Notice: Subject to any disclaimer, the term of this patent is extended or adjusted under 35 U.S.C. 154(b) by 613 days.

(21) Appl. No.: 17/266,909

(22) PCT Filed: Dec. 19, 2019

(86) PCT No.: PCT/SG2019/050624
§ 371 (c)(1),
(2) Date: Feb. 8, 2021

(87) PCT Pub. No.: WO2020/130946
PCT Pub. Date: Jun. 25, 2020

(65) Prior Publication Data
US 2021/0341414 A1   Nov. 4, 2021

(30) Foreign Application Priority Data
Dec. 21, 2018  (SG) .......................... 10201811538S

(51) Int. Cl.
*G01N 27/414* (2006.01)
*G01N 27/333* (2006.01)
*G01N 33/00* (2006.01)

(52) U.S. Cl.
CPC ....... *G01N 27/4141* (2013.01); *G01N 27/333* (2013.01); *G01N 33/004* (2013.01)

(58) Field of Classification Search
CPC . G01N 27/4141; G01N 27/333; G01N 33/004
See application file for complete search history.

(56) References Cited

U.S. PATENT DOCUMENTS

2010/0139365 A1* 6/2010 Fix ..................... G01N 27/4141
73/23.31
2011/0260219 A1   10/2011 Wahl et al.
(Continued)

FOREIGN PATENT DOCUMENTS

| CN | 106233481 A | 12/2016 |
|---|---|---|
| EP | 2639847 A1 | 9/2013 |
| EP | 3045902 A1 | 7/2016 |

OTHER PUBLICATIONS

International Search Report for PCT/SG2019/050624, Issued Mar. 9, 2020.
(Continued)

*Primary Examiner* — Peter M Albrecht
(74) *Attorney, Agent, or Firm* — NORTON ROSE FULBRIGHT US LLP; Gerard A. Messina

(57) ABSTRACT

A transistor for detecting gases in the ambient air. The transistor includes a plurality of electrodes with one electrode being a gate electrode. At least one electrode is individually coated by a ceramic. An ionogel connects all electrodes with each other, the ionogel being an ionic liquid immobilized by a matrix. The use of such a transistor as an air-quality sensor is described. A process for making the transistor is also described. The process includes providing a plurality of electrodes, wherein one of the electrodes is a gate electrode; individually depositing a ceramic precursor on at least one of the plurality of electrodes; and connecting the plurality of electrodes with an ionogel, the ionogel being an ionic liquid immobilized by a matrix. A transistor produced by the process is also described.

10 Claims, 12 Drawing Sheets

(56) References Cited

U.S. PATENT DOCUMENTS

2012/0273846 A1   11/2012  Neff et al.
2015/0323482 A1   11/2015  Shimoyama et al.
2017/0288280 A1* 10/2017  Shi .................... H01M 10/4235
2017/0370879 A1   12/2017  Aetukuri et al.

OTHER PUBLICATIONS

Marques Gabriel Cadilha et al., "Electrolyte-Gated Fets Based on Oxide Semiconductors: Fabrication and Modeling", IEEE Transactions on Electron Devices, IEEE Service Center, vol. 64, No. 1. 2017, pp. 279-285.

Leighton Chris, "Electrolyte-Based Ionic Control of Functional Oxides," Nature Materials, Nature Publishing Group, vol. 18, No. 1, 2019, pp. 13-18.

* cited by examiner

TRANSISTOR COMPRISING A CERAMIC AND AN IONOGEL

FIELD

The present invention relates to a transistor comprising a plurality of electrodes including one gate electrode for detecting gases in the ambient air.

BACKGROUND INFORMATION $CO_2$ is used as an analyte to measure indoor air quality. High $CO_2$ values can cause dizziness and headaches, which occur beside a lowered concentration capability. Therefore monitoring of $CO_2$ is emerging as a promising technology for smart control of heating, ventilation, and air conditioning (HVAC) systems and, e.g., on-demand ventilation.

Among several techniques for $CO_2$ sensing, most commonly used are optical (for example nondispersive infrared sensor), gravimetric (for example quartz crystal microbalance), acoustic (for example surface acoustic wave) and electrochemical techniques.

In the related art, the following problems with state-of-the-art electrochemical sensors or transistors are identified:

Firstly, there is a lack of sensors which meet most important key performance indicators (KPIs) of gas sensor development in terms of selectivity, sensitivity, stability. In particular for inorganic sensors, in most cases these are non-selective, have a low sensitivity, have high energy consumption, but have an easy readout. Hence, it is difficult to have chemical gas sensors which are absolutely selective to a single analyte. Almost all sensors show cross-sensitivity to at least relative humidity (RH), most likely also to chemically similar gases, e.g., to all reducing or oxidizing gases. It follows that in an environment with a complex composition of gases/vapours, there will always be the need to compensate for the response caused by contaminants. So far, most approaches in the related art ensure the accurate detection of a certain analyte by simply scaling up the number of sensors in an array of single-output sensors, which may result in high energy consumption, higher space requirement which prevents mobile application, and results in a high cost because investment scales almost linearly with number of sensors.

For organic sensors, conjugated systems are often used which are very stable. However, functional groups are often added to a conjugated backbone, which are most likely to cause performance degradation. In terms of hybrid sensors, the selectivity and sensitivity can be tuned by material combination. However, they often have stability issues, whereby the stability is governed by the 'weakest link in chain', which is usually the organic component.

Secondly, high energy consumption remains to be an issue. In particular, thin-film sensors based on inorganic materials are usually operated at 250-500° C., which causes high energy consumption even if the heater is operated in pulsed-mode. Additionally, no continuous measurement is possible with most sensors of the related art, but operation in pulsed mode may limit device lifetime due to power peaks occurring upon switching on/off.

Thirdly, the concept of one sensor per analyte has to be avoided due to limited space inside a mobile device, as even Micro-Electro-Mechanical Systems (MEMS) devices have limitations in down-sizing/miniaturization and the multi-variable sensing concept is state-of-the-art.

Fourthly, the functional film of a gas sensor or transistor only accounts to a fraction of the total cost of a sensor, which means that the Application-specific integrated circuit (ASIC) is the most significant price-determining factor. Lastly, complicated readout methods should be avoided.

In view of the above, there is a need for a material or a combination of materials for transistors which can overcome, or at least ameliorate, some of the problems discussed above.

SUMMARY

In a first aspect of the present invention, there is provided a transistor for detecting gases in the ambient air. In accordance with an example embodiment of the present invention, the transistor comprises a plurality of electrodes with at least one electrode of the plurality of electrodes being a gate electrode. Further, at least one electrode of the plurality of electrodes is individually coated by a ceramic. An ionogel connects all electrodes with each other, the ionogel being an ionic liquid immobilized by a matrix.

In a second aspect of the present invention, there is provided use of a transistor as described above as an air-quality sensor.

In a third aspect of the present invention, there is provided a process (100) for making a transistor. In accordance with an example embodiment of the present invention, the process comprises:

provide a plurality of electrodes, wherein at least one of the electrodes is a gate electrode (110);

individually depositing a ceramic precursor on at least one of the plurality of electrodes (130); and connecting the plurality of electrodes with an ionogel, the ionogel being an ionic liquid immobilized by a matrix (140). The process (100) may optionally comprise a method (200) for the deposition of the ceramic precursor.

In a fourth aspect of the present invention, there is provided a transistor produced by the process (100) as described above.

DETAILED DESCRIPTION OF EXAMPLE EMBODIMENTS

Figure 1:
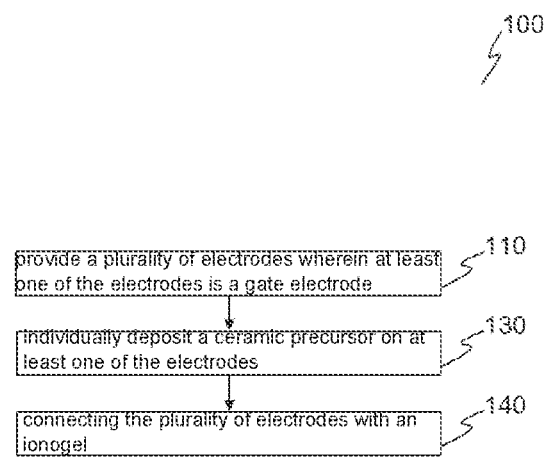
FIG. 1 shows a process flow chart of a process in accordance with an example embodiment of the present invention.

FIG. 1 is a process flow chart describing the individual method steps of the process 100, defined as follows: In step 110, a plurality of electrodes is provided, wherein one of the electrodes is a gate electrode. In step 130, a ceramic precursor is individually deposited on at least one of the plurality of electrodes. In step 140, the plurality of electrodes is being connected with an ionogel, the ionogel being an ionic liquid immobilized by a matrix.

Figure 2:
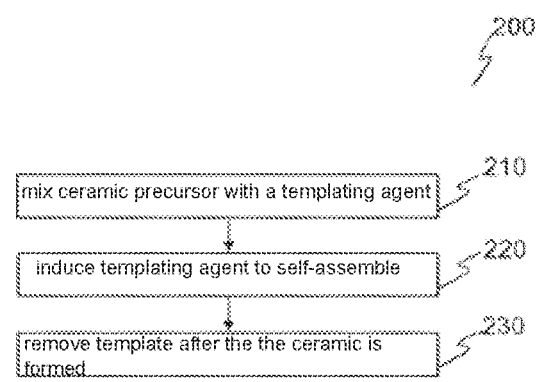
FIG. 2 shows a process flow chart of a process in accordance with an example embodiment of the present invention.

FIG. 2 is a process flow chart describing the individual method steps of the method 200, defined as follows: In step 210, a ceramic precursor may be mixed with a templating agent, optionally in an organic solvent. In step 220, the templating agent is then induced to self-assemble. In step 230, the template is removed after the ceramic formed, in order to release the porous ceramic in a heat treatment.

Figure 3:
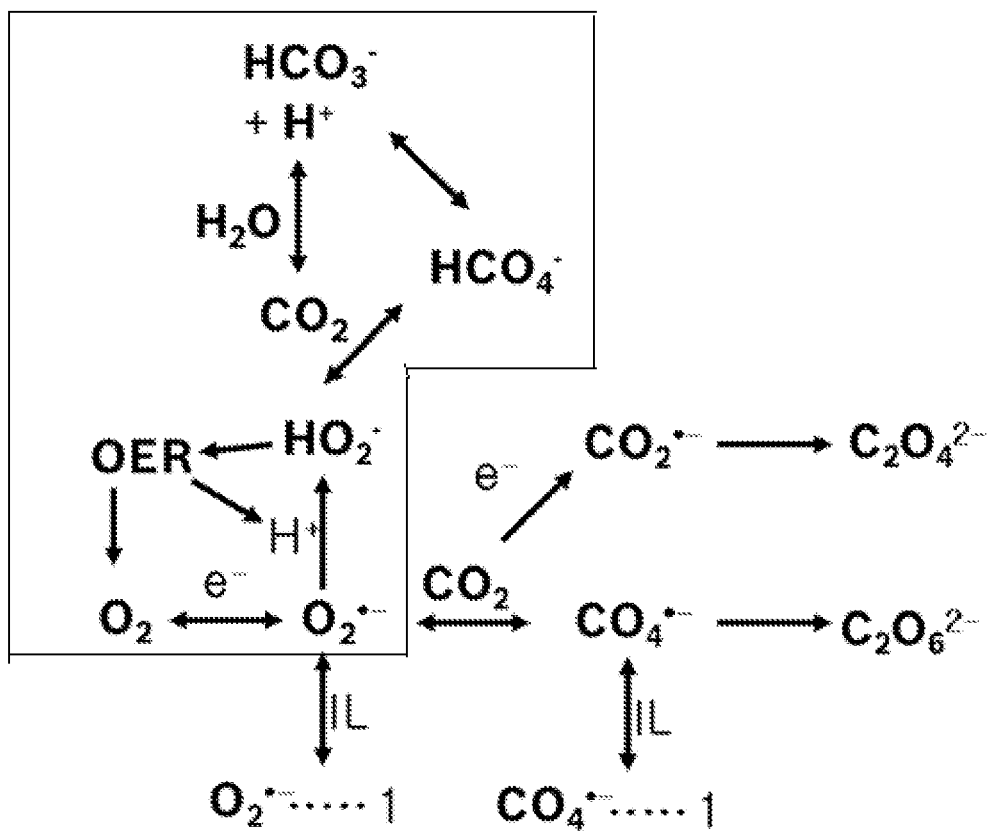
FIG. 3 shows schematically a sensing mechanism for carbon dioxide.

FIG. 3 shows schematically the sensing mechanism for carbon dioxide. The mechanism of reduction of carbon dioxide in the presence of oxygen using an ionic liquid electrolyte is supportive towards ionic liquid sensor developments. The relevant reactions, because of their reversibility and the availability of excess protons in the ionic liquid, are shown in a box. "1" refers to a suitable cation to be paired with the shown anion. As indicated, the most likely reaction pathway is the reversible formation of a hydroperoxyl anion ($HO_2^-$) which reacts with $CO_2$ to yield peroxymonocarbonate ($HCO_4^-$). "OER" is short for oxygen evolution reaction, which can either be the oxidation of water or hydroperoxyl/peroxymonocarbonate anions to dioxygen and protons. "IL" is short for ionic liquid.

Figure 4:
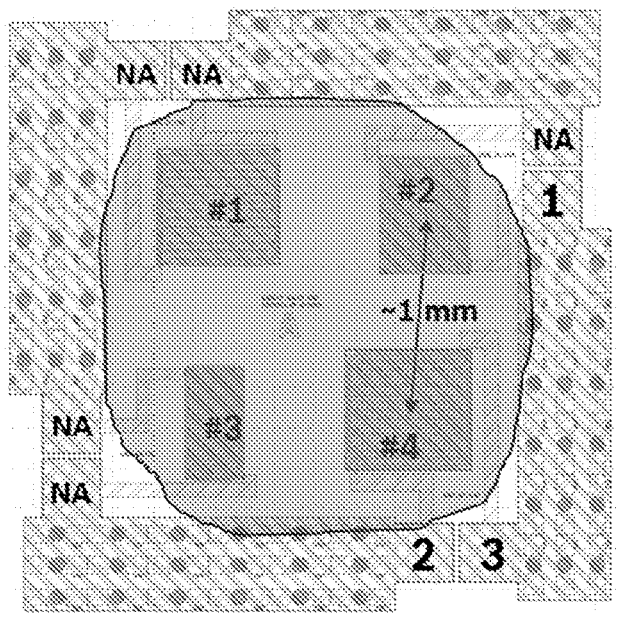
FIG. 4 schematically shows a chip with four interdigitated electrodes, whereby each interdigitated electrode is individually coated by the ceramic, optionally a metal oxide, in accordance with an example embodiment of the present invention.

FIG. 4 schematically shows a chip with four interdigitated electrodes, whereby each interdigitated electrode is individually coated by the ceramic, optionally a metal oxide. A single ionogel layer is covering all interdigitated electrodes shown as grey area covering numbers "#1" to "#4". The additional numbers refer to the type of electrode. "1" refers to the gate, indicating that this is the gate electrode. "2" refers to the "source" of the source-drain electrode, while "3" refers to the "drain" of the source-drain electrode. "NA" indicates "not applicable".

Figure 5:
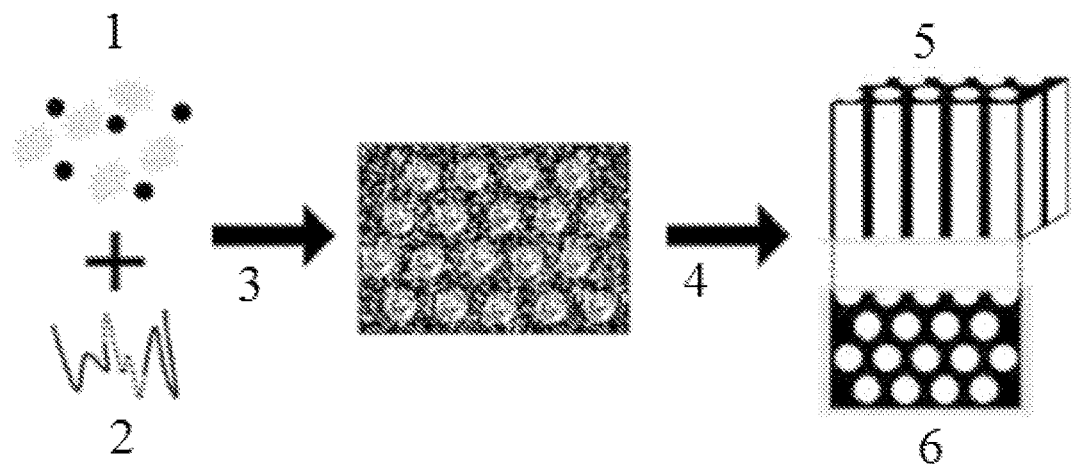
FIG. 5 schematically shows a soft-templated sol-gel route for obtaining (meso)porous ceramic films, optionally metal oxide films.

FIG. 5 schematically shows a soft-templated sol-gel route for obtaining (meso)porous ceramic films, optionally metal oxide films. In FIG. 5, "1" refers to the ceramic precursor. "2" refers to the templating agent. "3" refers to the self-assembly of the mixture of ceramic precursor and templating agent. "4" refers to the sintering, while "5" and "6" show the obtained, porous ceramic, in side view and in top view, respectively.

Figure 6A:
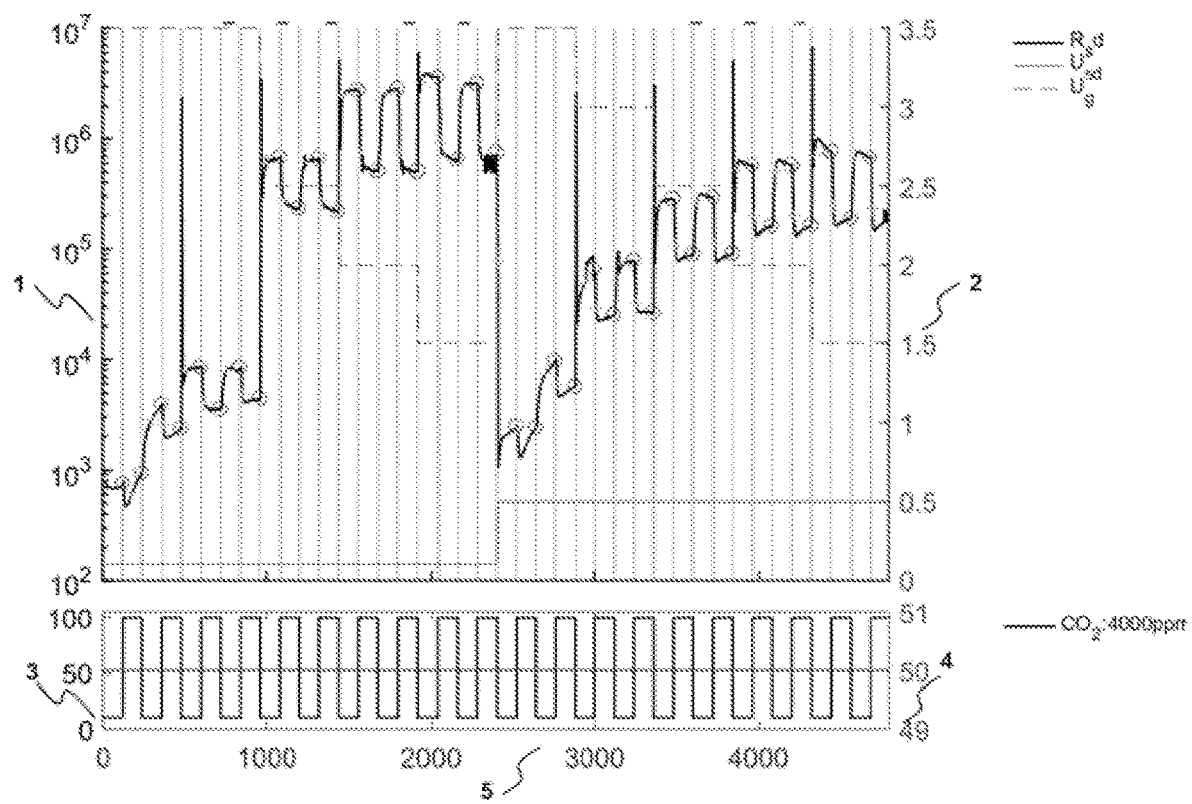
FIG. 6A shows the carbon dioxide response using the electrolyte-gated transistor (EGT) mechanism at various potentials, showing a variation of applied source-drain resistances.

FIG. 6A shows the carbon dioxide response using the electrolyte-gated transistor (EGT) mechanism at various potentials, showing a variation of applied source-drain resistances. The results are described in Example 4. In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %) and 5 is time (s).

Figure 6B:
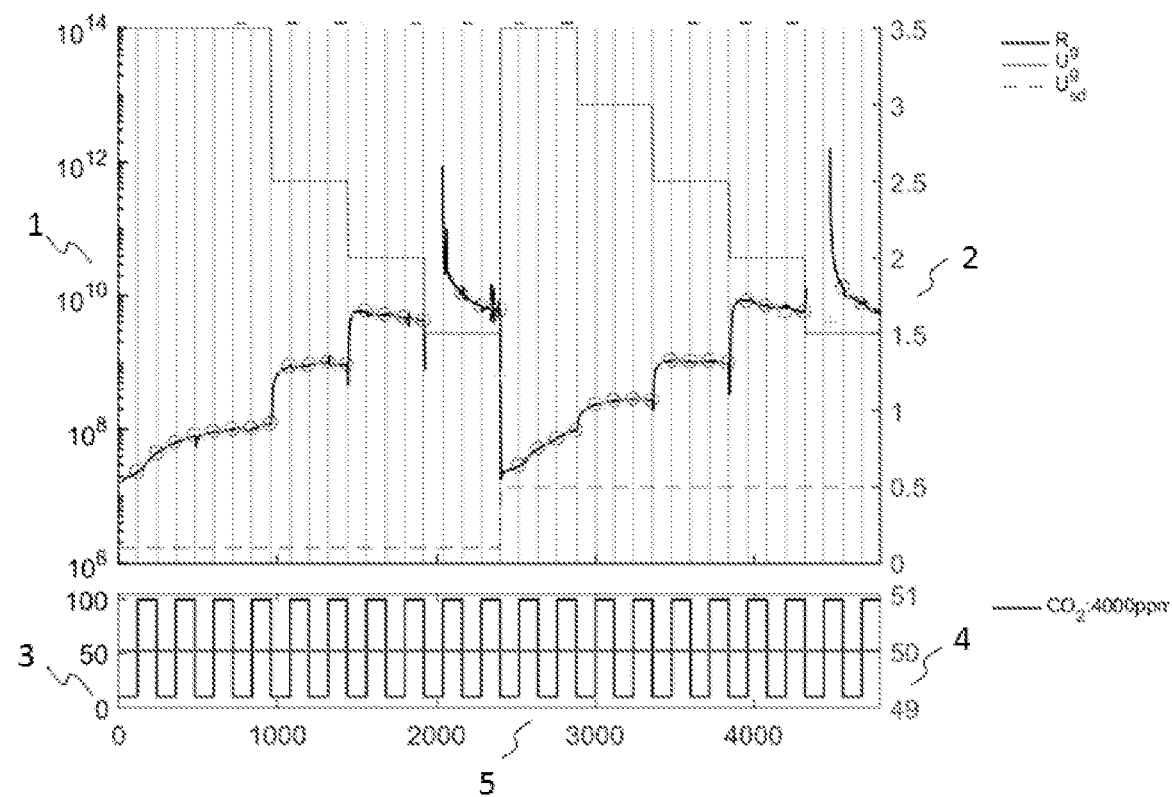
FIG. 6B shows the carbon dioxide response using the EGT mechanism at various potentials, showing a variation of applied gate resistances.

FIG. 6B shows the carbon dioxide response using the EGT mechanism at various potentials, showing a variation of applied gate resistances. The results are described in Example 4. In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %) and 5 is time (s).

Figure 7:
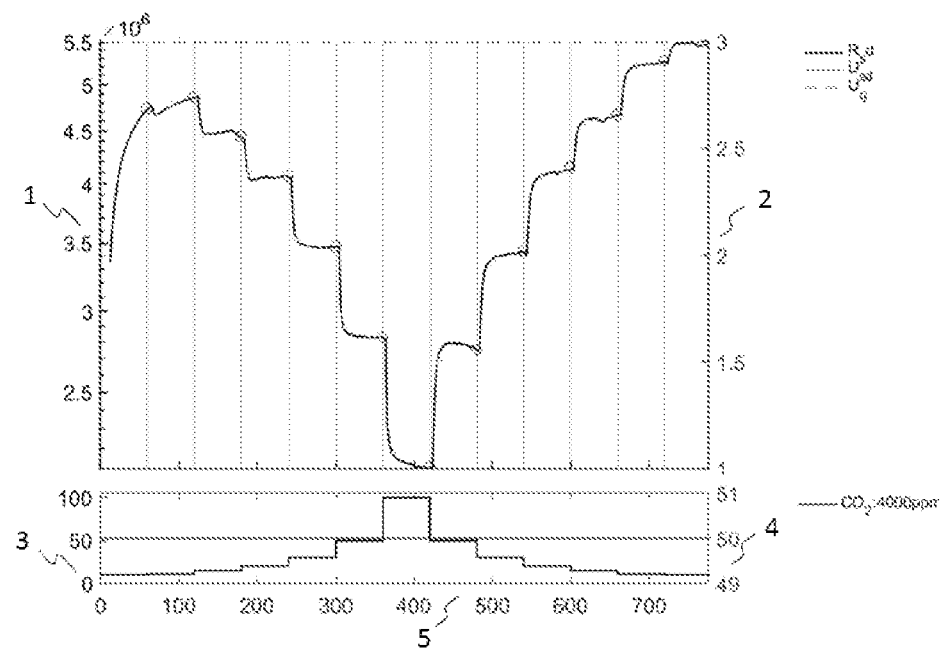
FIG. 7 shows the hysteresis of the transistor.

FIG. 7 shows the hysteresis of the transistor. The results are described in Example 5. In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %) and 5 is time (s).

Figure 8:
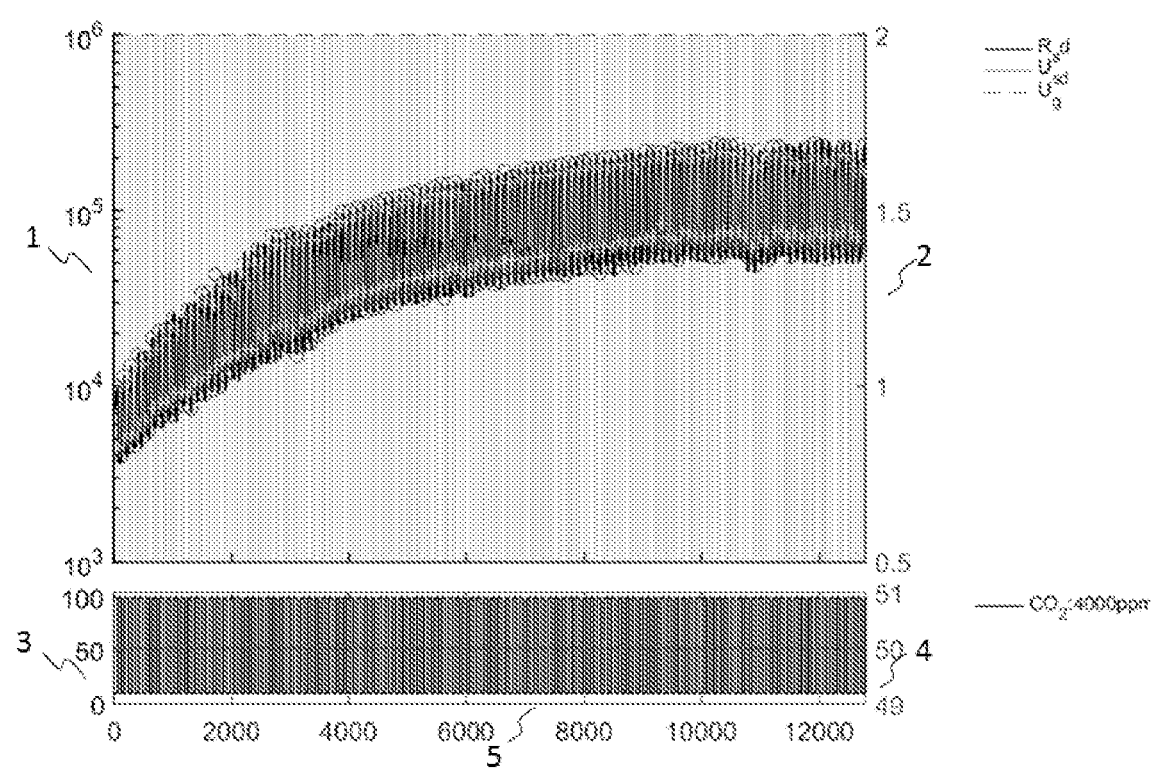
FIG. 8 shows the long-term stability.

FIG. 8 shows the long-term stability. The results are described in Example 6. In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %) and 5 is time (s).

Figure 9A:
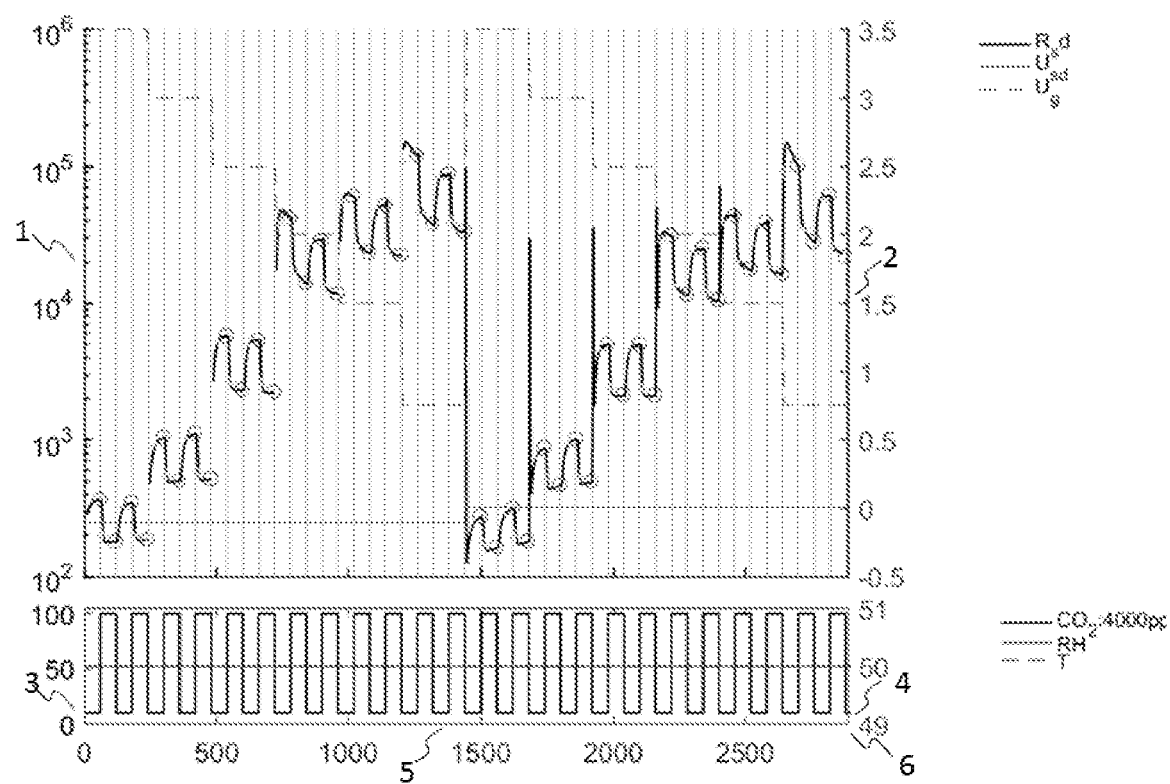
FIG. 9A shows the resistance measured for a transistor at varying concentrations of gases wherein the ceramic is exemplified with $In_2O_3$, doped with 1 at % of zinc (Example 7).

FIG. 9A shows the resistance measured for a transistor at varying concentrations of gases wherein the ceramic is exemplified with $In_2O_3$, doped with 1 at % of zinc (Example 7). In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 6, wherein 1 is IDE resistance (Ohm), 2 is Potential (V), 3 is Gas (%), 4 is relative humidity (RH, %), 5 is time (s) and 6 is temperature (° C.).

Figure 9B:
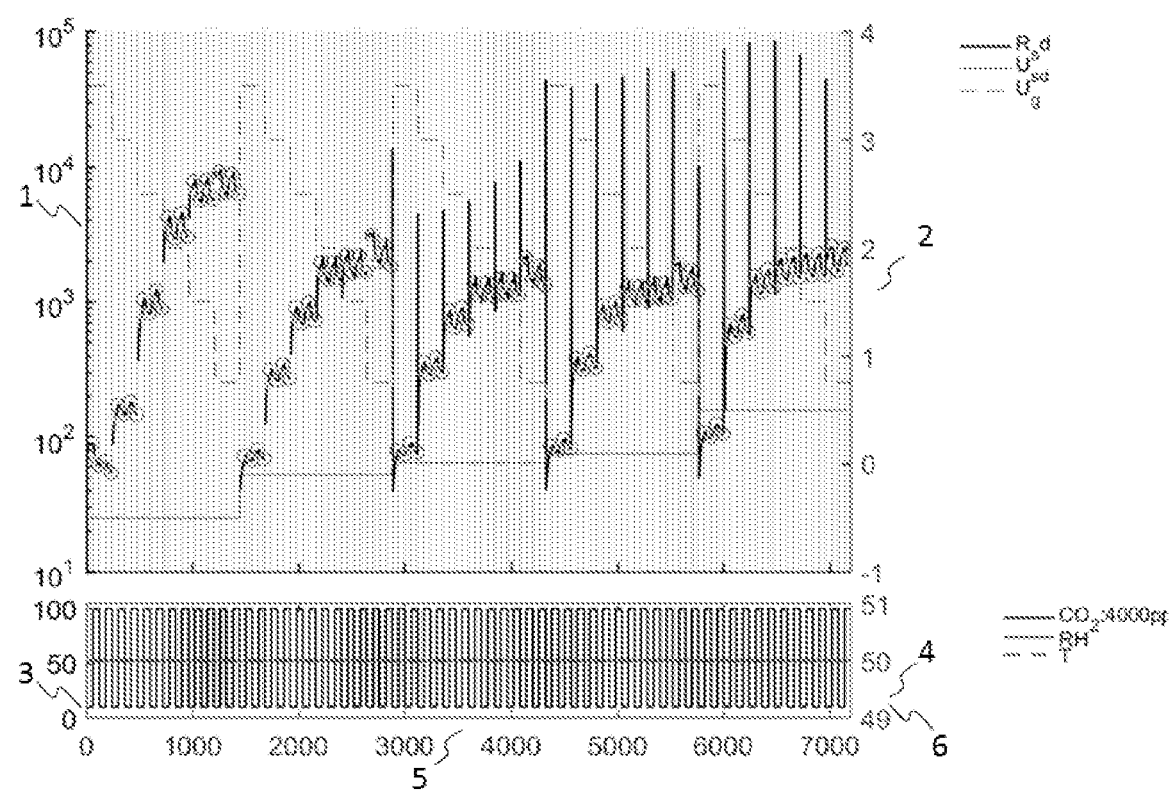
FIG. 9B shows the resistance measured for a transistor at varying concentrations of gases wherein the ceramic is exemplified with $SnO_2$ (Example 7).

FIG. 9B shows the resistance measured for a transistor at varying concentrations of gases wherein the ceramic is exemplified with $SnO_2$(Example 7). In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 6, wherein 1 is IDE resistance (Ohm), 2 is Potential (V), 3 is Gas (%), 4 is relative humidity (RH, %), 5 is time (s) and 6 is temperature (° C.).

Figure 10:
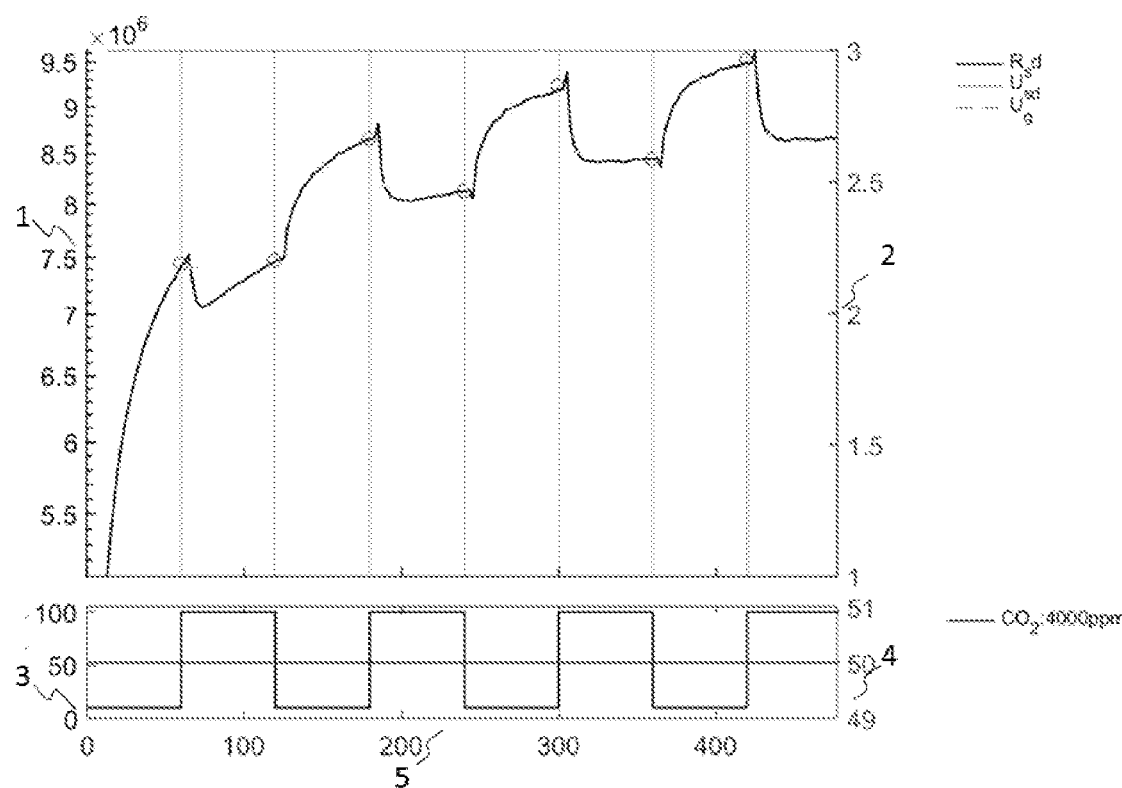
FIG. 10 shows the resistance measured for a transistor at varying concentrations of gases wherein the ceramic is absent and only the ionogel is present (Example 8).

FIG. 10 shows the resistance measured for a transistor at varying concentrations of gases wherein the ceramic is absent and only the ionogel is present (Example 8). In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %) and 5 is time (s).

Figure 11:
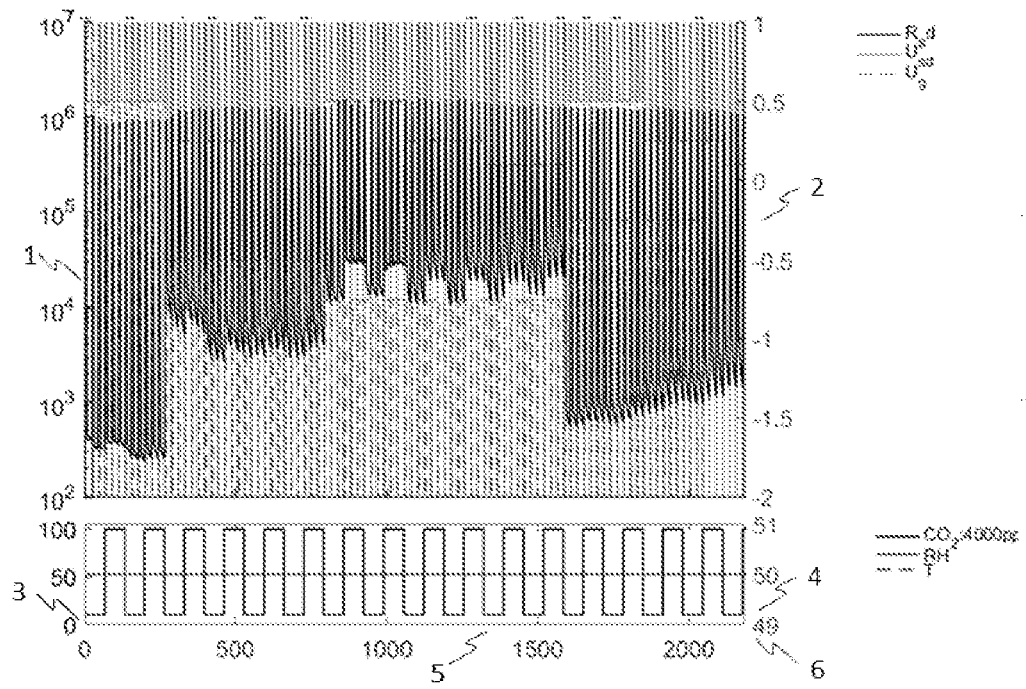
FIG. 11 shows the carbon dioxide response using the electrical double layer (EDL) mechanism at various potentials, applied to the source-drain IDE and the gate electrode.

FIG. 11 shows the carbon dioxide response using the electrical double layer (EDL) mechanism at various potentials, applied to the source-drain IDE and the gate electrode. The results are described in Example 9. In particular, FIG. 11 is an example for a measurement, which was carried out by pulsing the IDE electrode with 3 different potentials (E1, E2 and E3) at T=50° C. and RH=50%. $CO_2$ concentrations of 400 and 4000 ppm in synthetic air are purged alternately for 60 s. The height of the potential steps is indicated by the grey curves (right axis). A $CO_2$ concentration of 4000 ppm corresponds to a gas flow of 100% in the lower plot (black). For easier analysis, only the current during the $3^{rd}$ potential step is plotted. The captions on the graph are numbered from 1 to 6, wherein 1 is IDE resistance (Ohm), 2 is Potential (V), 3 is Gas (%), 4 is relative humidity (RH, %), 5 is time (s) and 6 is temperature (° C.).

Figure 12A:
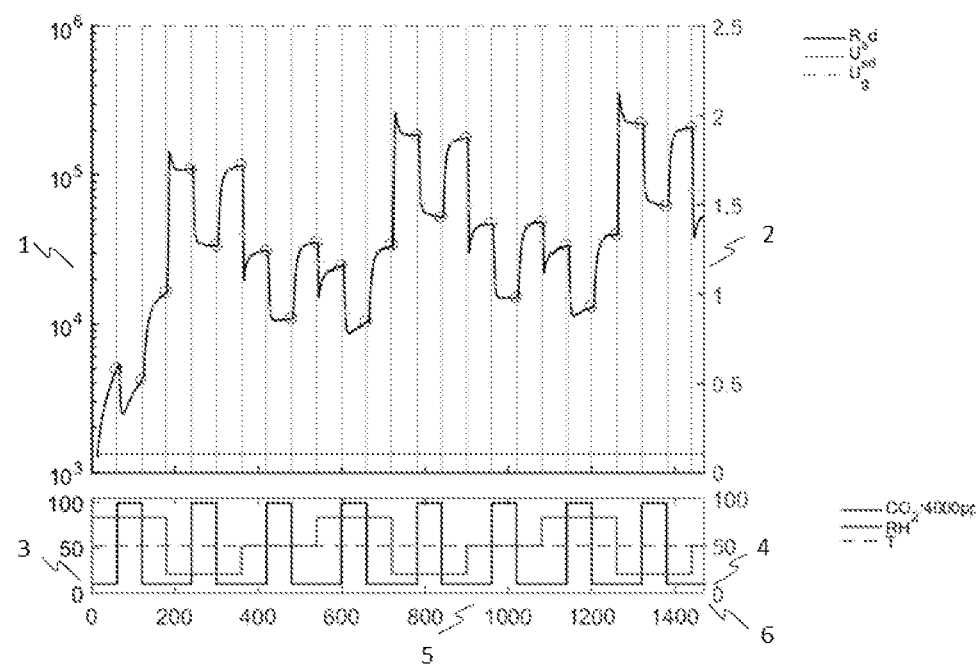
FIG. 12A shows the carbon dioxide response (400/4000 ppm) of the source-drain electrode at various RH (80%/20%/50%).

FIG. 12A shows the carbon dioxide response (400/4000 ppm) of the source-drain electrode at various RH (80%/20%/50%). The results are described in Example 10. In particular, FIG. 12A shows the resistance measured for a transistor at varying concentrations of $CO_2$ gas (400/4000 ppm), relative humidity (80%/20%/50%), and at an operation temperature of 50° C. In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 6, wherein 1 is IDE resistance (Ohm), 2 is Potential (V), 3 is Gas (%), 4 is relative humidity (RH, %), 5 is time (s) and 6 is temperature (° C.).

Figure 12B:
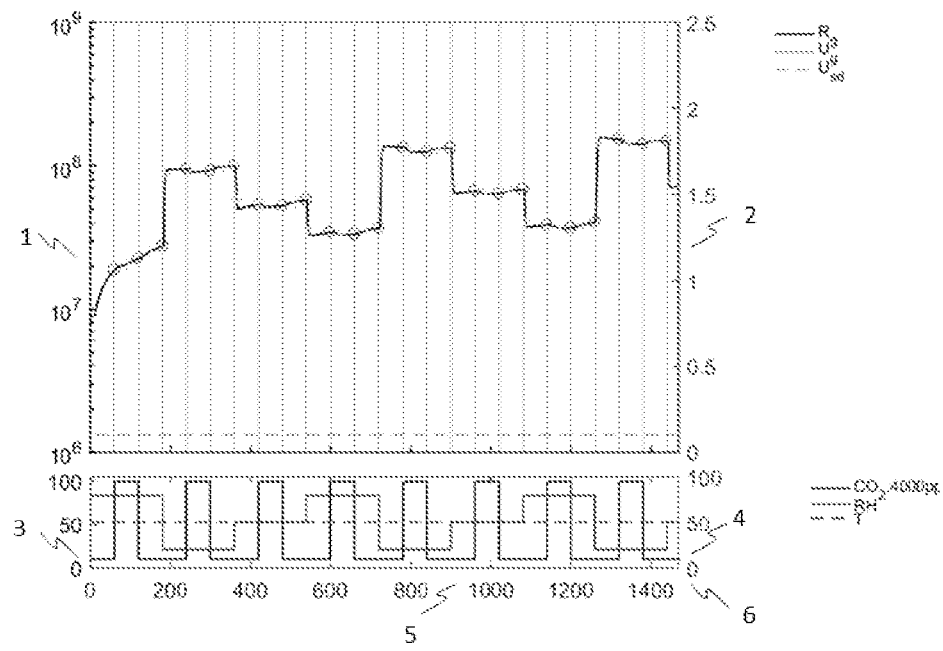
FIG. 12B shows the carbon dioxide response (400/4000 ppm) of the gate electrode at various RH (80%/20%/50%).

FIG. 12B shows the carbon dioxide response (400/4000 ppm) of the gate electrode at various RH (80%/20%/50%). The results are described in Example 10. In particular, FIG. 12B shows the resistance measured for a transistor at varying concentrations of $CO_2$ gas (400/4000 ppm), relative humidity (80%/20%/50%), and at an operation temperature of 50° C. In the upper plot, the resistance of the gate electrode is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 6, wherein 1 is IDE resistance (Ohm), 2 is Potential (V), 3 is Gas (%), 4 is relative humidity (RH, %), 5 is time (s) and 6 is temperature (° C.).

Figure 13A:
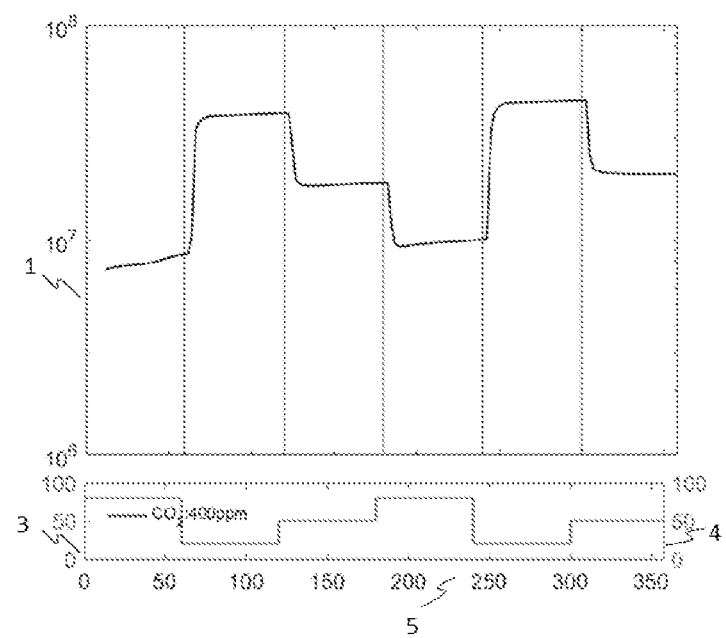
FIG. 13A shows the response of the gate electrode to RH (80%/20%/50%) at 50° C.

FIG. 13A shows the response of the gate electrode to RH (80%/20%/50%) at 50° C. The results are described in Example 10. In particular, FIG. 13A shows the resistance measured for a transistor at varying concentrations of $CO_2$ gas (400/4000 ppm), relative humidity (80%/20%/50%), and at an operation temperature of 50° C. In the upper plot, the resistance of the gate electrode is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity. The captions on the graph are numbered from 1 to 4, wherein 1 is IDE resistance (Ohm), 2 is Potential (V), 3 is Gas (%), and 4 is relative humidity (RH, %).

Figure 13B:
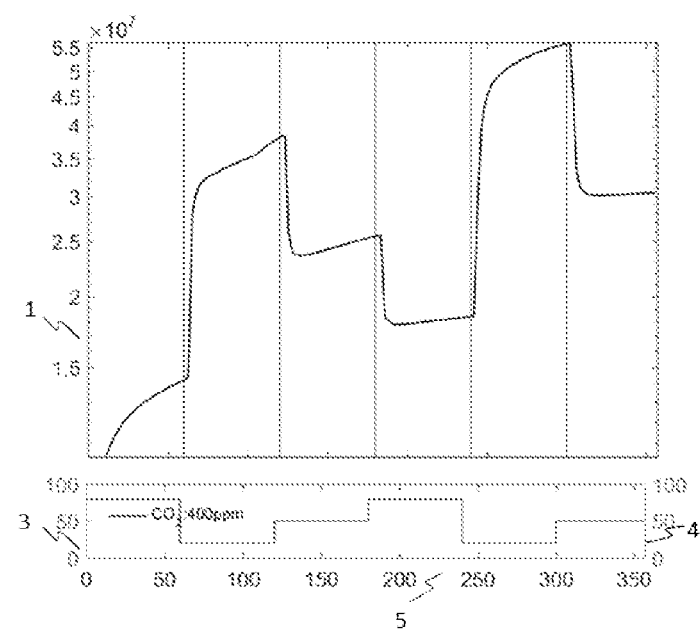
FIG. 13B shows the response of the gate electrode to RH (80%/20%/50%) at 75° C.

FIG. 13B shows the response of the gate electrode to RH (80%/20%/50%) at 75° C. The results are described in Example 10. In particular, FIG. 13B shows the resistance measured for a transistor at varying concentrations of $CO_2$ gas (400/4000 ppm), relative humidity (80%/20%/50%), and at an operation temperature of 75° C. In the upper plot, the resistance of the gate electrode is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity. The captions on the graph are numbered from 1 to 4, wherein 1 is IDE resistance (Ohm), 2 is Potential (V), 3 is Gas (%), and 4 is relative humidity (RH, %).

Figure 14A:
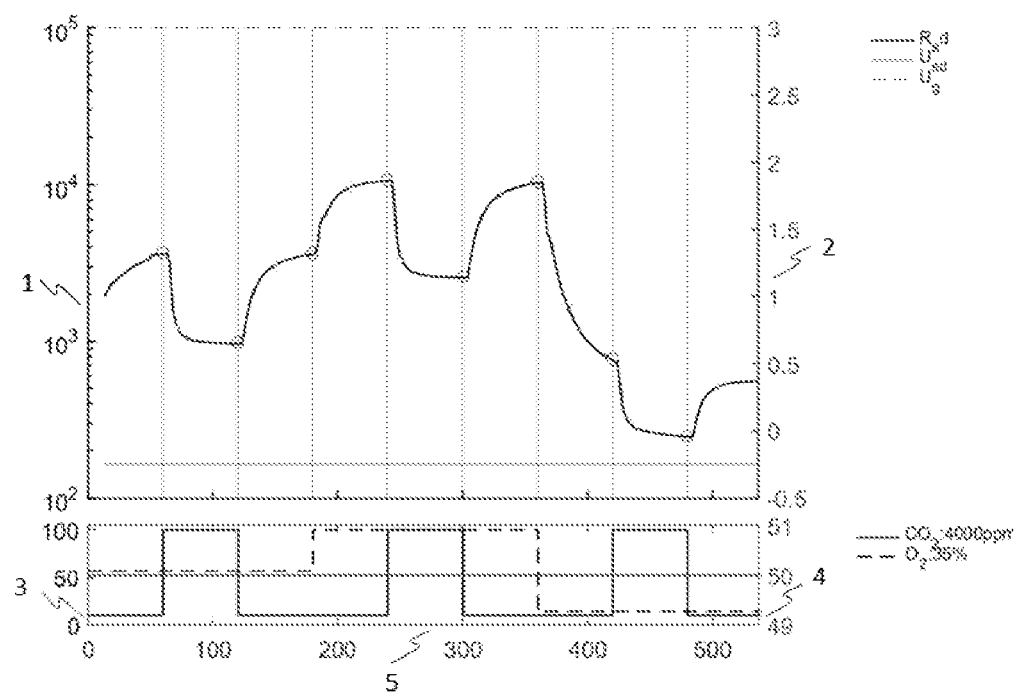
FIG. 14A shows the carbon dioxide response (400/4000 ppm) of the source-drain electrode at various $O_2$ concentrations (20%/30%/5%).

FIG. 14A shows the carbon dioxide response (400/4000 ppm) of the source-drain electrode at various $O_2$ concentrations (20%/30%/5%). The results are described in Example 11. In particular, FIG. 14A shows the resistance measured for a transistor at varying concentrations of $CO_2$ gas (400/4000 ppm), oxygen concentration (20%/35%/5%), relative humidity 50% and operation temperature 50° C. In the upper plot, the resistance of the material on the IDE is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %), and 5 is time (s).

Figure 14B:
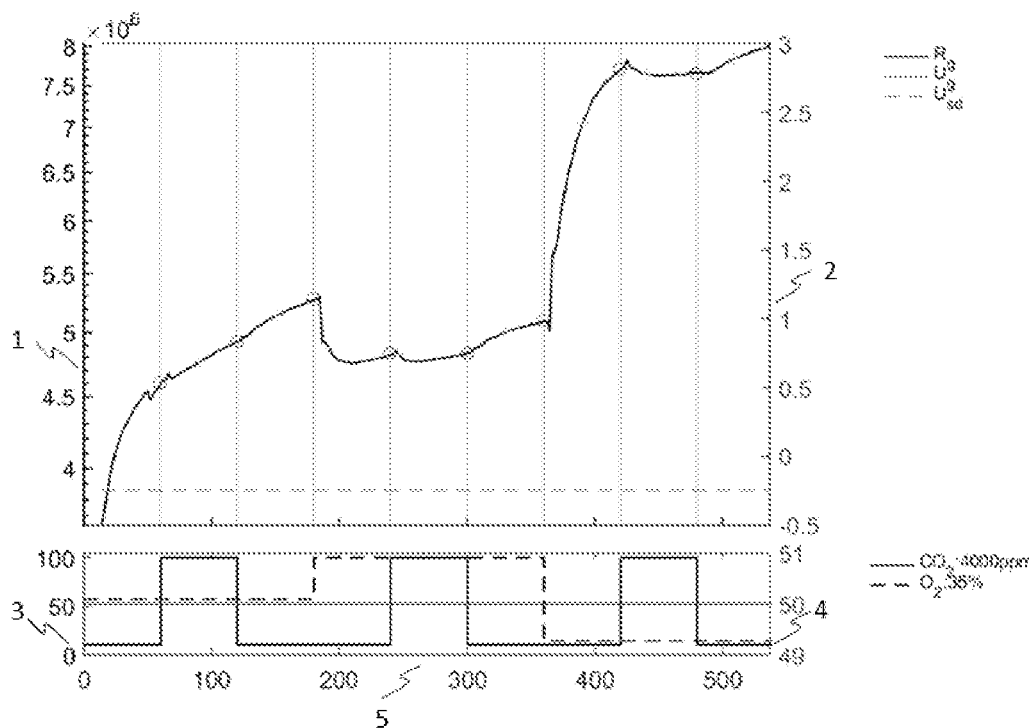
FIG. 14B shows the carbon dioxide response (400/4000 ppm) of the gate electrode at various $O_2$ concentrations (20%/30%/5%).

FIG. 14B shows the carbon dioxide response (400/4000 ppm) of the gate electrode at various $O_2$ concentrations (20%/30%/5%). The results are described in Example 11. In particular, FIG. 14B shows the resistance measured for a transistor at varying concentrations of $CO_2$ gas (400/4000 ppm), oxygen concentration (20%/35%/5%), relative humidity 50% and at an operation temperature of 50° C. In the upper plot, the resistance of the gate electrode is indicated by the thick solid curve, and gate and source-drain potentials are indicated by thin-solid and thin-dashed curves, respectively. In the bottom plot, the solid black curve indicates $CO_2$ concentration, the solid gray curve indicates relative humidity, and the dashed gray curve indicates the operating temperature. The captions on the graph are numbered from 1 to 5, wherein 1 is IDE resistance (Ohm), 2 is Potential (V), 3 is Gas (%), 4 is relative humidity (RH, %), and 5 is time (s).

Figure 15:
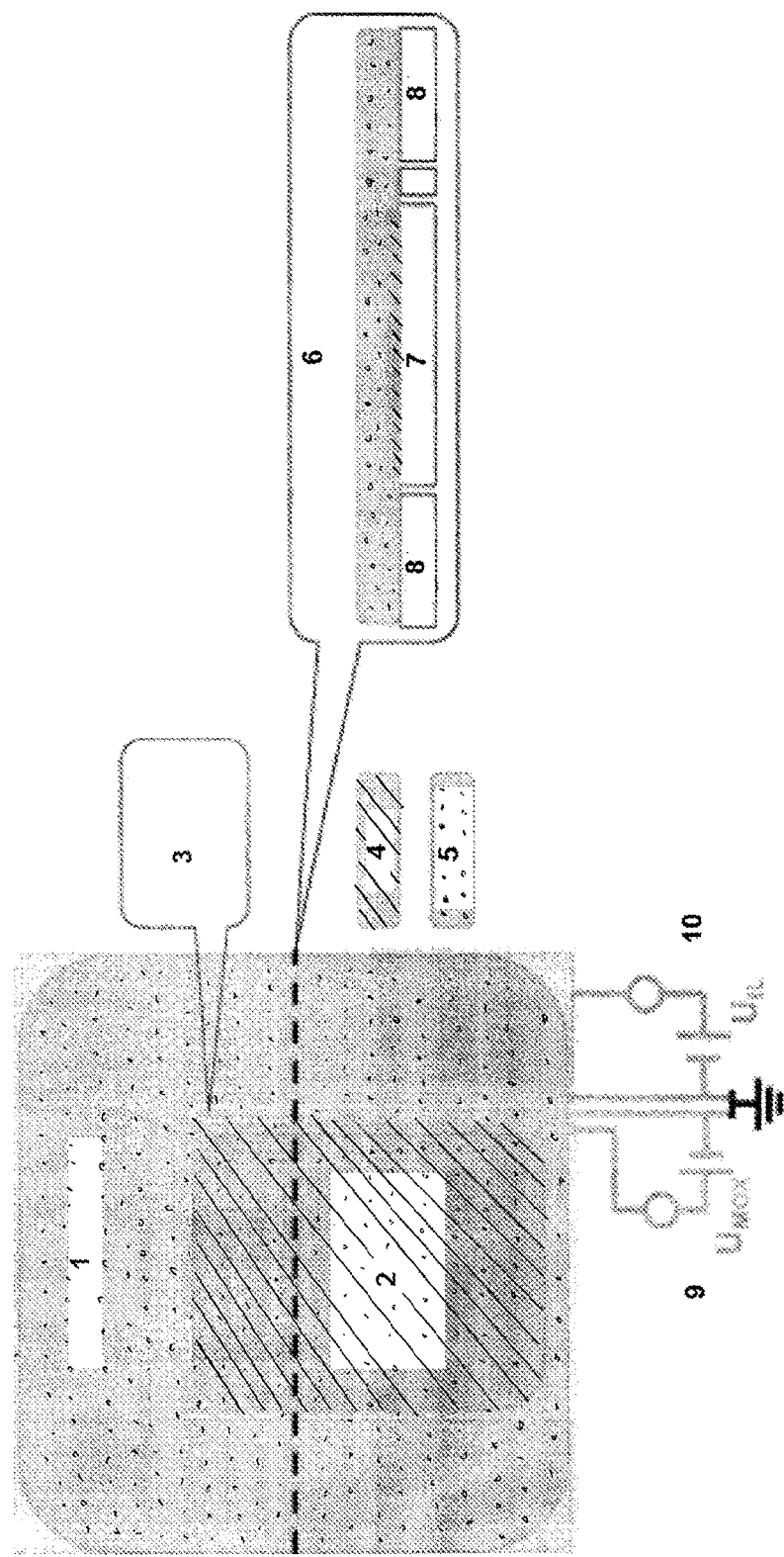
FIG. 15 shows an example transducer layout for multi-analyte sensing with the disclosed transistor (MOX@Ionogel) for simultaneous sensing of oxygen, humidity and the desired analyte

FIG. 15 shows an example transducer layout for multi-analyte sensing with the disclosed transistor (MOX@Ionogel) for simultaneous sensing of oxygen, humidity and the desired analyte ($CO_2$, $CH_4$, ethylene, etc.). In FIG. 1, "1" refers to the location of the gate electrode, "2" refers to the location of a pair of source-drain electrodes and "3" refers to an ionogel working electrode. "4" refers to the visualization of the location of the ceramic (optionally metal oxide), which is shown as skewed lines. "5" refers to the visualization of the location of the Ionogel, which is shown as dots. "6" shows a cross section of the dotted line, wherein "7" refers to the IDE and "8" refers to the gate. Using the same visualization as referred to in "4" and "5", it can be seen that the IDE is coated by the ceramic, while the gate electrode is not. All of the electrodes are connected to each other by a layer of the ionogel.

A solution to the above mentioned problems is provided by the transistor disclosed herein. Accordingly, in one aspect of the present invention, there is provided a transistor for detecting gases in the ambient air comprising a plurality of electrodes. At least one electrode of the plurality of electrodes is a gate electrode. At least one electrode of the plurality of electrodes is individually coated by a ceramic, wherein an ionogel is connecting all electrodes with each other. The ionogel is an ionic liquid immobilized by a matrix.

Firstly, the transistor, or composite of transistor, meets most important KPIs, which have been addressed in the introductory section. Furthermore, the transistor, as disclosed in the first aspect, is selective towards certain analytes, depending on solubility of this analyte in the employed ionic liquid. The transistor shows higher sensitivity and higher signal-to-noise ratio than most organic and inorganic materials. The long-term stability of the electrode composite solely depends on thermal stability and evaporation of ionic liquid, which have been proven to survive reflow-soldering conditions (in $N_2$ atmosphere).

Secondly, the transistor was shown to be operable in the temperature range 25 to 100° C. The transistor can be operated at room temperature (RT), which further lowers energy consumption and allows higher measurement rate Additionally, operation at elevated room temperature (~50° C.) is recommended in order to reduce cross-sensitivity to relative humidity (RH) and increase the insensitivity towards temperature variations of the atmosphere.

Thirdly, the transistor can be used in multi-variant sensing due to its unique temperature dependent sensitivity towards RH and $CO_2$. In particular, at low operation temperature, the sensor can be used as RH-sensor, and at elevated temperature as $CO_2$ sensor. Hence, simultaneous operation of only the ionogel and a ceramic-coated electrode with ionogel on the same transducer by certain electrode configurations can be used for multi-analyte sensing in order to eliminate cross-sensitivity. The transistor, having at least one electrode coated with a ceramic, and whereby all of the electrodes are connected with an ionogel, can be operated at two different sensing mechanisms, which show different dependence on RH and temperature. The transistor can therefore be tuned to detect various analytes. Pure Ionogel can furthermore be used either as $O_2$-sensor or RH-sensor by adjusting the operation temperature and the IDE/gate potentials.

Fourthly, the sensor can be operated as simple transistor in the resistance range 100-10,000 Ohm, which are favourable conditions for the development of an ASIC.

The "gate electrode" refers to an electrode typically used in transistors. It serves to control the electrical current between the source and the drain. The gate electrode is one electrode of the plurality of electrodes. The transistor can be electrochemically or electrostatically gated.

A ceramic coats at least one electrode of the plurality of electrodes. The "ceramic" may be a binary or ternary ionic compound, wherein at least one element is a metal and one other element is oxygen, nitrogen or carbon. The other element may therefore be present in the form of an oxide, nitride or carbide. In some embodiments, the ceramic may be a metal oxide. The metal oxide may consist exclusively of a metal and an oxide. The metal may be selected from alkali metals, transition metals, metalloids, lanthanoids, actinoids and post-transition metals, which may refer to the metallic elements in the periodic table located between the transition metals (to their left) and the metalloids (to their right). The post-transition metals may include gallium, indium, thallium, tin, lead, bismuth and aluminum. The metal oxide may be selected from a mixture between two or more types of metal oxides, for example $La_2O_3$—$SnO_2$. The mixture may be obtained either by doping (incorporation of dopants into crystal structure of host metal oxide) or loading (two distinct phases contacting each other). Preferably, the metal oxide is selected from $La_2O_3$—$SnO_2$, $WO_3$, $In_2O_3$, $TiO_2$, $ZnO$, $SnO_2$, $BaTiO_3$, $BaSnO_3$, or a mixture thereof. In another embodiment, a metal oxide of a particular conductivity may be employed, such that the electric conductivity of the metal oxide has to be greater than the ionic conductivity of the ionic liquid, otherwise domination of the "ionic liquid" reaction mechanism may occur. In another embodiment, the metal oxide may have moderate sintering temperatures because high temperature metal oxide (MOX) phases are undesired due to incompatibility with integrated circuit (IC) fabrication. In another embodiment, all metal oxides may be employed, which have a conductivity that is governed by oxygen vacancies or oxygen-species concentration on the MOX surface. In another embodiment, p- or n-type conducting MOX may be employed. These may be chosen from either pure oxides or mixed oxides of metals such as tin (Sn), indium (In), titanium (Ti), aluminum (Al), strontium (Sr), gallium (Ga), lanthanum (La). In another embodiment, MOX may be used which can form carbonates on the surface, for example from rare earth metal oxides, such as cerium (Ce), lanthanum (La), gadolinium (Gd), europium (Eu), Neodynium (Nd). In another embodiment, some main group elements may be used for the MOX, such as alumina, silicon or lead.

The ceramic may further comprise a dopant. The doping material may be an elemental transition metal, post transition metal or metalloid. In one embodiment, the dopant may be selected from zinc, tin and antimony. In one example, the dopant is zinc. The dopant may be contained in the metal in up to 20 atomic %, or up to 10 atomic %, or up to 5 atomic %, or up to 3 atomic %, or up to 1 atomic %. Preferably, the concentration may be elected such that the conductivity remains high.

In some embodiments of the present invention, the ceramic may be coated with a noble metal. The noble metal may be selected from the group consisting of ruthenium (Ru), rhodium (Rh), palladium (Pd), silver (Ag), osmium (Os), iridium (Ir), platinum (Pt), and gold (Au). The reason for coating the ceramic with a noble metal may be to enhance catalytic activity. In such a way, it may be possible to use a spill-over effect in order to increase the sensitivity of the ceramic towards variation of $O_2$-species concentration in the ionic liquid.

The ceramic may be provided in a porous form. The porosity of the ceramic may be obtained by a templated sol-gel method (see FIG. 2 and FIG. 5). In various embodiments, the porosity is an "open porosity", meaning that the pores should have an opening in order to be accessible to gases. The pores may be wide enough to be impregnated by viscous liquid, for example the ionic liquid, but as small as possible in order to yield a high surface area.

Alternatively, the ceramic may be deposited as (non-porous) ultra-thin film (<50 nm) via various physical and chemical deposition techniques, which however may decrease the sensitivity compared to a porous thin film. In some embodiments, the porous thin ceramic film may have a thickness of more than about 50 nm, optionally more than 100 nm, optionally between about 100 and about 1000 nm, optionally between about 100 and about 800 nm, optionally between about 100 and about 600 nm, optionally between about 100 and about 500 nm.

As mentioned before, in some embodiments of the present invention, the ceramic is porous, which may help in providing a large surface area. Therefore, in preferred embodiments, the ceramic may be in a form which provides a high porosity, such as for example in the form of nanoparticles. In other embodiments, the ceramic is deposited by sputtering or chemical vapor deposition (CVD). In another embodiment, cracking and delamination in the ceramic film should be prevented in order to ensure a closed electrically conductive path in between electrode fingers. According to various embodiments, a change of porosity of the ceramic could increase kinetics of reaction and sensitivity (surface area).

The choice of ceramic and modification may be considered in view of the following aspects and adapted accordingly: Electrical conductivity, thermal coefficient of conductivity (optimal sensing temperature may be different for various ceramic, but only measured in narrow temperature-range), porosity, exposed surface planes, which $O_2$-species are adsorbed on surface, surface acidity, surface charge, $O_2$ vacancy defect concentration and $O_2$-species concentration on surface.

At least one electrode of the plurality of electrodes may comprise or substantially consist of a material selected from platinum, gold, silver, carbon, conducting polymers, a combination thereof. At least one of the electrodes may be a "source-drain" electrode, containing both the source and the drain. The distance between the source-drain electrode and the gate electrode may be up to about 5 mm, or up to about 3 mm, or up to about 2 mm, or between about 0.5 to about 5 mm, or between about 0.5 to about 3 mm, or between about 0.5 to about 2 mm, or between about 0.5 to about 1.5 mm, or about 1 mm. The electrodes may be interdigitated electrode (IDE) structures. The plurality of electrodes may be 2, 3 or 4 electrodes.

As mentioned above in the first aspect, an ionogel is connecting all electrodes with each other, wherein the ionogel is an ionic liquid immobilized by a matrix. The matrix may be a polymer matrix, in which case it may be selected from an organic polymer matrix. Alternatively or additionally, it may be a macromolecular and/or a supramolecular matrix. The macromolecular matrix may be selected from chitin, cellulose, gelatin, PEG, and other polymers. In case of a supramolecular matrix, the matrix material may be selected from aspartame-derivatives and/or cholesterol-derivatives. In general, any matrix may be selected as long as it is capable of gelating the ionic liquid and immobilizing it accordingly. In yet another embodiment, the matrix may comprise nanoparticles. Such nanoparticles matrixes may be selected from colloid materials, for example, from $SiO_2$, $SnO_2$ or $TiO_2$ nanoparticles. By "connecting" is meant that the ionogel covers the plurality of electrode and thereby provides for ionic conductivity across the transistor.

In a preferred embodiment, the matrix may be a polymer matrix, optionally an organic polymer matrix, optionally selected from fluoropolymer-copolymers, conducting polymers, organosilicons, polyethers and acrylates. In particular, the polymer may be selected from the group consisting of poly(vinylidene fluoride-co-hexafluoropropylene (PVDF-HFP), polyaniline (PANT), a blend of poly(ethylene oxide)/polyacrylonitrile/poly(methyl methacrylate)/poly(vinylidene fluoride), polydimethylsiloxane (PDMS) and a sulfonated tetrafluoroethylene based fluoropolymer-copolymer (Nafion). In one embodiment, the polymer matrix may be poly(vinylidene fluoride-co-hexafluoropropylene (PVDF-HFP) and/or Nafion. Poly(vinylidene fluoride-co-hexafluoropropylene (PVDF-HFP) and/or Nafion as polymers may be chosen as they provide an optimal thermal stability and solution processability. In one example, the matrix is Nafion.

The term "ionic liquid" (IL) refers to salts that are liquid over a wide temperature range, including room temperature. The ionic liquid used herein may be an organically based salt. The ionic liquid may be electrically not conductive. It may further be capable of dissolving $O_2$-species and the analyte of interest may be used to tune the selectivity towards this particular analyte type. In some cases, chemically similar molecules may probably be dissolved, too, which may cause cross-sensitivity. In some cases, the ionic liquid may simultaneously dissolve O2 species and the analyte of interest. In some cases, the ionic liquid may form a complex with the analyte on the ceramic surface while drawing electrons from the ceramic conduction band. Structurally, the ionic liquid may be a monomer, i.e., it does not contain covalently linked repeating units. Preferably, the organically-based salts may be, for example, imidazole derivatives, pyridine derivatives, pyrrolidine and pyridine derivatives. In a preferred embodiment, the ionic liquid may be a dialkylsubstituted imidazole derivative as cation, wherein the alkyl substituents are positioned at the nitrogen atoms. The alkyl substituents may be alkyl units selected from $C_1$-$C_5$. The counter anion may be selected from inorganic cations or organic cations. It may be selected from tetrafluoroborate ($BF_4^-$), hexafluorophosphate ($PF_6^-$), hexafluoroantimonate ($SbF_6^-$), nitrate, bisulphate (hydrogen sulphate), tetraphenylborate [$B(C_6H_5)_4^-$], thiocyanate, acetate, hexyltriethylborate, trifluoromethylsulphonyl, nonafluorobutanesulphonate, bis[(trifluoromethyl)sulphonyl] imide, tris[(trifluoromethyl)sulphonyl]methide, trifluoroacetate and heptafluorobutanate, as well as anions based on chlorides and other halides of aluminum, copper, manganese, lead, cobalt, nickel or gold, e.g., tetrachloroaluminate ($AlCl_4^-$), heptachlorodialuminate ($Al_2Cl_7^-$) and tetrachlorocuprate ($CuCl_4^{2-}$ and $CuCl_4^{3-}$), halogen anions, for example fluoride, chloride and bromide. Additionally or alternatively, a mixture of ionic liquids may be employed. Additionally or alternatively, the ionic liquid may be provided in form of an acid, which may enable new reaction mechanisms of the ionic liquid with $CO_2$. In one example, the ionic liquid is 1-ethyl-3-methylimidazolium tetrafluoroborate ([EMIM] [BF4]). 1-Ethyl-3-methylimidazolium tetrafluoroborate as ionic liquid may be chosen as this ionic liquid provides optimal results regarding $CO_2$ sensing and is electrically not conductive. Since IL-based sensors are based on electrochemical principles, it is necessary to know about possible Faradaic reactions. $O_2$ has been found to be reduced at −1.4V to −1.2V vs. a pseudo-reference electrode (Pt). Electrochemical reduction of $CO_2$ to CO occurs in the range 1.5V to 2.5V. Minor Faradaic reactions are expected to occur in the range of gate potential used to operate the transistor. Any potential within stability window of employed ionic liquid may be chosen. However, the best gate potential strongly depends on employed ionic liquid, ceramic and transducer layout (gate electrode & IDE).

The ionic liquid immobilized in the matrix, as mentioned above, may form an ionogel. This ionogel may be characterized in that there is no covalent bond between the ionic liquid and the matrix. The ionogel may be electrically not conducting but may be a good ionic conductor. The ionogel may be deposited on top of the individually sintered ceramics coated on the plurality of electrodes. This allows exploiting the properties of the ionic liquid, while at the same time providing mechanical stability. The ionic liquid may be homogenized with the matrix. Further, by providing the ionic liquid in a matrix, the ionogel may be instrumental for the diffusibility of gases due to the porosity of the matrix, and optionally the porosity of the ceramic. In particular, the permeability of the ionogel for gases is improved compared to using a pure ionic liquid, as the pure ionic liquid would have a higher viscosity. For example, a gas would be able to diffuse in the interfacial regions between the pore wall of the matrix and the ionic liquid.

In a second aspect, there is provided use of a transistor as described above as an air-quality sensor. The use of the air-quality sensor may comprise a method of detection of a gas. The gas may be $O_2$, $NO_2$, $SO_2$, $H_2S$, CO, or $CO_2$, preferably $CO_2$. Without being bound to theory, it is believed herein that the detection method is based on operation as an electrolyte-gated transistor which converts the chemical detection of the gas into modulation of the resistance of the channel material. The modulation of the electronic states in the channel material may be achieved either by electrostatic gating or electrochemical gating. Which gating method to use depends on many factors, among which are: targeted analyte, employed ionic liquid and metal oxide, as well as the transducer layout (gate electrode & IDE).

In a third aspect of the present invention, there is provided a process (100) for making a transistor, the process comprising:
  providing a plurality of electrodes, wherein at least one of the electrodes is a gate electrode (110);
  individually depositing a ceramic precursor on at least one of the plurality of electrodes (130); and
  connecting the plurality of electrodes with an ionogel, the ionogel being an ionic liquid immobilized by a matrix (140).

The process (100) may comprise a first step of providing a plurality of electrodes. The plurality of electrodes may be deposited on a chip. At least one or each electrode may be individually coated by the ceramic. The coating process may proceed with a templated sol-gel-method (200). Alternatively, the ceramic may be deposited by inkjet printing, screen-printing or gravure printing, dip-coating and similar thin-film deposition techniques. In embodiments, wherein the deposition is a templated sol-gel-process (200), and as illustrated in FIG. 2 and FIG. 5, a ceramic precursor may be mixed with a templating agent (210), optionally in an organic solvent. The templating agent is then induced to self-assemble (220). During self-assembly, the templating agent forms a porous network, which may be a free-standing 3D network. The term "3D network" is to be interpreted broadly to include a substantially stable framework which is porous and may be a template. The porous network may be classified by the size of the pores. They can be classified either as micro- and meso-porous or macro-porous. The porous nature of the template may serve the function of being a "negative" in the deposition process for the ceramic. Hence, any material may be used, as long as it undergoes self-assembly and is removable by a heat treatment. The 3D network according to the present invention may comprise or substantially consist of a macromolecule or a macromolecule microsphere. The ceramic may grow on the pore walls of the template. The template may therefore be infiltrated by the ceramic, resulting in a porous ceramic. Thereby, the ceramic may adapt the morphology of the template.

The "organic solvent" used in the precursor solution may be a polar aprotic solvent. The polar aprotic solvent may be selected from the group consisting of tetrahydrofuran, ethyl acetate, acetone, dimethylformamide (DMF), acetonitrile, dimethyl sulfoxide, nitromethane or propylene carbonate, and a combination thereof. In one embodiment, the solvent may be non-toxic and environmentally friendly. In one example, the solvent may be DMF.

In an alternative embodiment or additional embodiment, the "organic solvent" used in the precursor solution may be an apolar solvent. The apolar solvent may be selected from the group consisting of cyclopentane, hexane, cyclohexane, benzene, toluene, 1,4-dioxane, chloroform, diethyl ether or dichloromethane. The apolar solvent may be used as a minor solvent in order to tune the porosity of the templating agent by swelling the apolar phase of the formed micelles. The apolar solvent may be mixed with the polar aprotic solvent in order to form the organic solvent.

The template may be a "sacrificial" template, i.e., it may be removed after the ceramic formed in order to release the porous ceramic in a heat treatment. The heating treatment may therefore essentially be sintering. This sintering treatment may convert the precipitated ceramic precursor into the ceramic structure (230).

During the sol-gel method (200), the porosity of the template can be adjusted. As the ceramic adopts the morphology of the template, adjusting the porosity may lead to higher sensitivity of the ceramic for the detection of gases by tuning the dimension of the ceramic. This may result in a lower conductivity of the ceramic, but a higher sensitivity with a smaller diameter in the material. Hence, this process represents an in situ formation of a thin film of composite material with tunable porosity, for example on an MEMS IDE by a sol-gel process.

The ceramic precursor may have a metal component. The metal component of the ceramic precursor may be a different compound from the ceramic of the sensor. The metal component may be any metal source from which the final ceramic may be obtained. Hence, any source of metal ions may be used, provided it can form a ceramic by (post-) processing. In the event the metal component is a metal salt, it may be provided as an organometallic precursor, for example as acetate, citrate, acetylacetonate, alkoxide, and a combination thereof. Alternatively, it may be provided as an inorganic precursor, for example as an oxide, nitrate, sulphide, phosphate, halogenide (especially chloride), and a combination thereof. If a metal salt is used as the precursor, this compound may be provided as a hydrate. In one example, indium nitrate was used.

The templating agent may be a soft templating agent selected from a macromolecule. (Meso)porosity of the base layer may be achieved by using soft-templating agents, such as PMMA microspheres, CTAB, SDBS, poloxamers, PEO-PB-PEO and PVDF-TrFE-CTFE. Exemplary, Pluronic F127 was used. Hard templates as often utilized in literature reports are avoided due to harsh conditions during their removal for the creation of free-standing porous MOX, which could deteriorate the MEMS.

Once the templated ceramic precursor, embedded in the templating matrix, is sintered, it turns into the ceramic to be used in the first aspect. As mentioned above, at least one of the plurality of electrodes may be individually covered by the produced ceramic film. Alternatively, at least two, or at least 3, or at least four electrodes may be covered by this ceramic film. In one example, all of the electrodes of the plurality of electrodes are individually covered by a ceramic film as described above.

Subsequently, the ionogel layer may be deposited, connecting the plurality of electrodes (140), whereby the ionic liquid may infiltrate the pores of the porous ceramic. The ionogel may be dissolved in a solvent. The ratio of the ionic liquid to the matrix in the ionogel may be 1:4-4:1, or 1:2-2:1, or 1:1. The deposition technique of the ionogel may comprise dropcasting, ink-jet printing, screen-printing or gravure printing, preferably dropcasting. In the presence of a solvent, the solvent may subsequently be evaporated. The evaporation may comprise heating the ionogel to about 50° C. to 300° C., optionally 100° C. to 200° C., or approximately 150° C. The evaporation time may be about 5 min to about 1 h, or about 10 min to about 30 min, or approximately 15 min. The evaporation may at the same time anneal the transistor.

In one embodiment, the transistor may be placed on a microhotplate. Hence, the heater may be based on a microhotplate MEMS structure. Alternatively, ceramic heaters may be used to heat the device during operation or regeneration.

In a fourth aspect of the present invention, there is provided a transistor produced by the process (100) as disclosed above.

One of the proposed solutions presented herein is an electrolyte-gated transistor (EGT). The proposed gas sensing concept can be applied to any analyte which will react with a superoxide radical (or any other ionic oxygen species available) within an ionic liquid. This reaction will deplete the concentration of adsorbed oxygen species on the surface of a ceramic, optionally a metal oxide, causing its conductivity to change (reaction mechanism shown in FIG. 3). In one embodiment, the transducer may have a 3-terminal layout, wherein 2 terminals are connected via a film of metal oxide. Another terminal may be connected to the above-mentioned MOX layer via a film containing ionic liquid. The ionic liquid may be immobilized by a matrix (for example Nafion). The only electrical-conductive connection between the MOX-coated electrodes and the single electrode may be via an external circuit and power source.

The role of the ionic liquid is believed to be as follows: The ionic liquid provides sensitivity and selectivity towards $CO_2$, which is obtained by choosing an ionic liquid which preferably absorbs $CO_2$, i.e., the adsorption ratio for $CO_2$ compared to other gases such as $CH_4$, $SO_2$, etc. is very high. The ionic liquid therefore may act as a diffusion barrier for contaminants which could alter the conductivity of the ceramic film, optionally MOX film, whereas the contaminant, for example, may be $NO_2$ and $In_2O_3$, for example, may be the ceramic.

The ionic liquid should be able to stabilize (undefined) oxygen-species (peroxo radical, etc.) in order to increase the probability to react with absorbed $CO_2$. The potential applied to the gate-electrode is considered to be far too positive (2.0 to 3.0V) to trigger reduction of $O_2$ species, potentially regenerating irreversibly reacting $O_2$-species, which may be a hint towards the reversibility of the reactions occurring within the ionic liquid. If, however, the potential of the gate-electrode is chosen to be too high (>2.5V), unwanted side reactions may occur. These unwanted side reactions may include bubbling of the ionic liquid on the gate electrode. The unwanted side reactions may also be due to electrochemical decomposition of the ionic liquid or decomposition of all contaminants adsorbed from the atmosphere or residues from the synthesis because the electrochemical stability window might be exceeded.

The role of the ceramic, optionally MOX, is believed to be as follows: It is believed to not have a passive role, since sensing performance could not be increased when only two electrodes were coated independently by MOX and then connected via ionogel, as they behaved exactly the same way as if only ionogel was deposited in between two electrodes (understood from literature). Such an arrangement did not even facilitate electron transfer between electrode and analyte. Without being bound to theory, it is assumed that the depletion of oxygen species on the surface of the MOX is the reason for the variation of the conductivity. It is further proposed that the oxygen species react (reversibly) with $CO_2$ within the ionic liquid. Since the concentration of $CO_2$ in the ionic liquid depends on the $CO_2$ partial pressure in the surrounding atmosphere, the amount of $O_2$-species which are bound by $CO_2$ depends on the external $CO_2$ concentration. The potential applied to the MOX may not be sufficient to trigger faradaic reactions (−0.5 to 0.5V). It is assumed that the sensitivity is governed by the internal surface area of the ceramic, optionally metal oxide, having an interface to the ionic liquid.

According to various embodiments concerning the readout, instead of using the ceramic resistance as observable for the measurement of the gas concentration, the gate potential may be monitored as function of gas concentration. For this, the gate potential might be adjusted in a feedback loop in order to keep the ceramic resistance constant. In another embodiment, electrochemical readout methods may be employed, e.g., chronoamperometry, impedance spectroscopy, cyclic voltammetry of both, gate- and source-drain electrodes. In another embodiment, the sensor may be operated either isothermally at various temperatures or in pulsed mode, where the heater is only turned on periodically. In another embodiment, the source-drain potential is chosen such that no significant $CO_2$ response is measured while the dependence of the resistance on $O_2$-concentration remains high. In such a case, the source-drain signal instead of the gate-signal can be used for $O_2$-sensing.

According to various embodiments concerning the transducer, a bottom gate-electrode beneath the source-drain IDE may be employed in order to tune conductivity of the ceramic. This may be useful for decreasing resistance of high resistance ceramic in order to make use of their unique surface chemistry. In another embodiment, the source-drain IDE layout may be varied. The main design variation may consist of changing channel length/width, electrode height and number of fingers. In another embodiment, the gate electrode layout may be varied. The main design variation consists of the total surface area being in contact with the IL and the distance to the source-drain IDE.

According to various embodiments, the transistor may have at least three electrodes in order to determine the concentration of RH, $O_2$ and the analyte $CO_2$. Two of the electrodes may be connected via a porous thin film of a metal oxide, whereby a layer of the ionogel may be coated on all three electrodes. The actual analyte can be sensed via two different sensing mechanisms. One mechanism is based on the formation of complexes between the analyte and ionic liquid species on the ceramic surface, involving electron transfer from the conduction band of the ceramic to the complex (EDL mechanism). Another mechanism is based on the fact that the analyte reacts with oxygen species from the ceramic surface, causing the release of trapped electrons back into the conduction band of the ceramic (EGT mechanism). The choice of sensing mechanism for determining the analyte concentration depends on the nature of the analyte and the properties of the ionic liquid. If the analyte is able to react with superoxide species within the ionic liquid, the EGT mechanism is preferred due to easier readout, higher stability and better sensitivity. If the analyte only can form complexes with the ionic liquid-species, the electrical double layer (EDL)-mechanism has to be applied. If the analyte can do both, react with superoxide and form complexes with IL-species, the application of both sensing mechanisms consecutively will improve the sensor performance. Intrinsic cross-sensitivity of ionic liquid towards RH and $O_2$ requires a way to compensate for the presence of these contaminants without employing separate sensors. By applying a suitable voltage between electrodes which are connected via the ionogel and adjusting the operation temperature, either the RH or the $O_2$-concentration can be determined. Water electrolysis and $O_2$-reduction occur at different potentials in ionic liquids. At higher temperature, the cross-sensitivity to RH is lower, allowing more accurate sensing of $O_2$-concentration.

The proposed transducer layout for a multi-sensing application of the transistor is shown in FIG. 15. The analyte ($CO_2$, $CH_4$, ethylene) is sensed by using gate and source-drain electrodes. The EGT mechanism may be used for analytes which react with superoxide within ionic liquid, causing a depletion of oxygen species on the surface of the ceramic (exemplary illustrated as MOX), resulting in the modulation of the MOX conductivity. The EDL mechanism may be applied for analytes which do not easily react with superoxide in ionic liquids but are more prone to form complexes with ionic liquid-cation on the MOX surface, modulating the MOX conductivity, by changing the depth of the depletion layer. The temperature should be chosen such that the cross-sensitivity to RH is negligible. $O_2$-sensing can be performed by using gate electrode (same potential as above) and single working electrode at a high temperature. RH-sensing can be performed by using gate and single working electrode at a low temperature. Instead of simple amperometric sensing of RH, Electrochemical Impedance Spectroscopy (EIS) techniques can be applied since the RH usually has a higher impact on capacity compared to conductivity.

EXAMPLES

Example 1

Device Fabrication—Choice of Electrodes

For the proof of the proposed concept, there were employed micromachined electrodes on a $Si/SiO_2$-wafer. The electrode for the present experiments was a "pseudo-reference electrode" (Pt). On each 3×3 mm chip, 4 IDE structures were deposited, as could be seen from FIG. 4. Each IDE structure is individually deposited by a metal oxide film. A film of ionogel (grey area in FIG. 4) is connecting all IDEs with each other. For the current measurements, IDE #4 was used as the source-drain IDE, and a single electrode of IDE #2 was used as the gate-electrode. IDE #4 consists of 14 fingers on each terminal. The finger length, the channel length and the finger width are 500 μm, 10 μm and 20 μm, respectively. IDE #2 consists of 14 fingers on each terminal. The finger length and the channel length are 500 μm, 10 μm and 30 μm, respectively. The distance between the centers of IDE #4 and IDE #2 is about 1000 μm.

Example 2

Device Fabrication—Choice of Ceramic

In this report, MOX films were obtained by a templated sol-gel method (see FIG. 5). For this, a mixture of In-nitrate precursor (4 mmol) and the soft-templating agent Pluronic F127 (500 mg) was dissolved in the solvent dimethylformamide (10 ml) at room temperature. The ink was deposited via drop-casting on the aforementioned electrodes. The freshly deposited films were kept for some time under dry nitrogen in order to induce the self-assembly of templating agent with inorganic precursor. After drying the films under dry atmosphere at ambient temperature, the films were heated up to 250° C. and held at this temperature for 30 min. Finally an additional heating step was applied in order to sinter the MOX films and to remove the templating agent. For this, the films were heated at 450° C. for 3 h. FIG. 5 shows schematically the process of the templates so-gel process as applied in this work. Tuning of film morphology/porosity is achieved by using different templating agents, mixture of solvents, conditions during self-assembly like temperature, humidity, etc.

Example 3

Device Fabrication—Choice of Ionogel

The employed ionic liquid is [EMIM][BF4], which is electrically not conductive. The ionic liquid (0.2 g) and a 20% Nafion dispersion in water (1.0 g) were dissolved in DMF (10 ml) at room temperature. The weight ratio Nafion/ionic liquid is 1/1. The ink was drop-casted on top of the sintered MOX film. After deposition, the devices were annealed at 150° C. for 15 min in order to evaporate the solvent.

In the following, the results of the templated sol-gel synthesis route for La-, Sn-, and In-ceramics are shown; all materials were deposited on the same reticle and processed under the same conditions, despite the fact that each material needs slightly different processing conditions in order to optimize its resulting phase. However, obtaining good results although the parameters are not optimized, proves the general applicability of the method to different metal oxide compounds.

Example 4

Optimization of Source-Drain and Gate-Potentials for $CO_2$ Detection by EGT Mechanism Experiments concerning the optimal potential of source-drain and gate electrode for $CO_2$ detection by EGT mechanism are illustrated in FIG. 6A and FIG. 6B. The results illustrate the carbon dioxide response at various potentials, showing a variation of applied gate and source-drain resistances. It was observed a high resistance of gate-electrode and a low resistance of source-drain interdigitated electrode (IDE). There was also observed a strong dependence of both resistances on the applied potentials, as well as a strong dependence of $CO_2$-sensitivity on the applied potentials. Although the $CO_2$ response of the source-drain IDE was very large, the gate-electrode shows no significant response, which indicates that $CO_2$ did not directly react on the gate electrode because the C in $CO_2$ already is in its highest oxidation state and electrolysis of $CO_2$ is unlikely at elevated room temperature. An increasing resistance of the source-drain IDE correlated with a decreasing current through the gate electrode, which could indicate that less (negatively charged) $O_2$-species are desorbed from the metal oxide and attracted by the gate electrode, where they are either adsorbed or oxidized (due to the positive potential of the gate electrode).

Example 5

Hysteresis

Experiments concerning the hysteresis of the transistor are illustrated in FIG. 7. After a short burn-in (~4 min), the sensor seemed to be fairly stable. There was a high stability of the sensor observed, as can be seen from the small difference between the resistance levels for the same $CO_2$ concentrations. Furthermore, the sensor showed a good resolution, as a clear distinction between the two lowest $CO_2$ concentrations (400 ppm and 450 ppm) was possible.

Example 6

Long-Term Stability

Experiments concerning the long-term stability of the transistor are illustrated in FIG. 8. It was observed that burn-in took about 9,000 s. A low drift and stable response was shown after burn-in. After switching the sensor off and on again, the drift was observed again. This means that the sensor should be operated in a continuous mode in order to keep the sensor signal stable. Continuous operation, as observed herein, was less of a problem compared to other materials due to the low power consumption.

Example 7

Various Ceramics and Their Observed Resistance Profiles

For this disclosure, different ceramic materials ($In_2O_3$ doped with 1 at % Zinc and $SnO_2$), in combination with the polymer matrix Nafion and the ionic liquid 1-ethyl-3-methylimidazolium tetrafluoroborate ([EMIM][$BF_4$]) were used. The observations of the transistor using the ceramics as discussed above are shown in FIG. 9A and FIG. 9B.

In the experiments, it was shown that $In_2O_3$, doped with 1 at % Zn (FIG. 9A), shows a higher sensitivity compared to $In_2O_3$. It was also shown that $SnO_2$ (FIG. 9B) shows lower sensitivity compared to $In_2O_3$. It may be seen that the baseline resistance and the $CO_2$ sensitivity strongly depend on the type of ceramic employed. The reason for differences between the ceramic may be manifold, ranging from different surface chemistry to different morphologies of the films.

Example 8

Only Ionogel

This transistor has been made without the presence of a ceramic. It was observed that there was a much lower response and higher resistance compared to the above ceramic/ionogel sensor. The response of pure Ionogel is pointing into the same direction as for ceramic/ionogel sensor. However, the sensing mechanisms are thought to be independent because the response of pure Ionogel is most likely caused by the direct electrochemical reduction of $CO_2$ to CO, whereas this reaction might only contribute very little to the overall sensitivity of transistor due to the small currents expected from this process.

Example 9

Optimization of Source-Drain and Gate-Potentials for $CO_2$ Detection by EDL Mechanism Experiments concerning the optimal potential of source-drain and gate electrode for $CO_2$ detection by EDL mechanism are illustrated in FIG. 11. The results illustrate the carbon dioxide response (400/4000 ppm) at various potentials applied to the source-drain IDE and the gate electrode. It was observed that analytes which cannot easily react with superoxide within the ionic liquid can be detected via an alternative sensing mechanism. This mechanism is supposedly based on the adsorption of complexes composed of the ionic liquid cation with the analyte on the MOX surface. The adsorption of the analyte molecule is accompanied with an electron transfer from the MOX, modulating the depletion zone, thus the conductivity of the MOX. With this sensing mechanism, there is an even higher dependence of the sensor performance of the applied potentials, claiming that best performance is achieved when the ionic liquid-cations are optimally arranged on the MOX surface at a certain potential.

Example 10

Relative Humidity (RH) Sensing

Experiments concerning the RH sensing are illustrated in FIG. 12A, FIG. 12B, FIG. 13A and FIG. 13B. The results show the carbon dioxide response (400/4000 ppm) at various RH (80%/20%/50%). A moderate dependence of baseline resistance of source-drain IDE on the RH is illustrated. There is only a small dependence of the $CO_2$ response of source-drain IDE on RH, whereas a higher response is observed at lower RH. A moderate dependence of baseline resistance of gate-electrode on RH is observed. From FIG. 13A and FIG. 13B it can be seen that by increasing the operation temperature from 50° C. to 75° C., the RH response of gate-electrode is reduced to about half Although the dependence of the $CO_2$ response on RH is small, the influence of the RH on the baseline resistance has to be corrected.

Example 11

Oxygen ($O_2$) Sensing

Experiments concerning the $O_2$ sensing are illustrated in FIG. 14A and FIG. 14B. The results illustrate an increased resistance with rising $O_2$-concentration at the source-drain IDE. At the gate-electrode, there was observed an increased (Faradaic) current with rising $O_2$-concentration. The baseline resistance of the source-drain IDE is significantly affected by change in $O_2$-concentration due to varying amount of electron-drawing $O_2$-species on the MOX surface. It follows that although the shown variation in $O_2$ concentration will never occur to this extent during expected use-case scenarios, a correction should be done with the knowledge of the $O_2$ concentration. Pure ionogel at high temperature can be used as $O_2$-sensor since the cross-sensitivity to RH decreases with rising temperature. Response to $CO_2$ is very small, thus the information on $O_2$-concentration can be used for the correction of the $CO_2$ sensor. An optimized potential for $O_2$ sensing is depending on the employed ionic liquid and transducer layout. It is possible to adjust the potential such that $CO_2$-cross-sensitivity is negligible. A value of −1.2V is agreed on in the related art to be the potential for the reduction of oxygen to superoxide.

The invention claimed is:

1. A transistor for detecting gases in ambient air, comprising:
 a plurality of electrodes, at least one electrode of the electrodes being a gate electrode, and at least one other electrode of the electrodes being individually coated by a ceramic;
 wherein an ionogel connects all of the electrodes with each other, the ionogel being an ionic liquid immobilized by a matrix.

2. The transistor as recited in claim 1, wherein the ceramic is porous.

3. The transistor as recited in claim 1, wherein the ceramic is a metal oxide.

4. The transistor as recited in claim 1, wherein at least one electrode of the plurality of electrodes includes a material selected from one or more of the following: platinum, gold, silver, carbon, conducting polymers.

5. The transistor as recited in claim 1, wherein the matrix includes a polymer selected from the group consisting of poly(vinylidene) fluoride-co-hexafluoropropylene (PVDF-HFP), polyaniline (PANI), poly(ethylene oxide)/polyacrylonitrile/poly(methyl methacrylate)/poly(vinylidene fluoride), a sulfonated tetrafluoroethylene based fluoropolymer-copolymer (Nafion).

6. The transistor as recited in claim 1, wherein the ceramic includes a dopant.

7. The transistor as recited in claim 1, wherein the ceramic is coated with a noble metal.

8. A method of using a transistor, comprising:
 providing the transistor, the transistor including a plurality of electrodes, at least one electrode of the electrodes being a gate electrode, and at least one other electrode of the electrodes being individually coated by a ceramic, wherein an ionogel connects all of the electrodes with each other, the ionogel being an ionic liquid immobilized by a matrix; and
 using the provided transistor as an air-quality sensor.

9. A process for making a transistor, the process comprising:
 providing a plurality of electrodes, wherein one of the electrodes of the plurality of electrodes is a gate electrode;
 individually depositing a ceramic precursor on at least one electrode of the plurality of electrodes, wherein at least one other electrode of the plurality of electrodes is individually coated by a ceramic; and
 connecting the plurality of electrodes together with an ionogel, the ionogel being an ionic liquid immobilized by a matrix.

10. A transistor produced by providing a plurality of electrodes, wherein one of the electrodes of the plurality of electrodes is a gate electrode, individually depositing a ceramic precursor on at least one electrode of the plurality of electrodes, wherein at least one other electrode of the plurality of electrodes is individually coated by a ceramic, and connecting the plurality of electrodes together with an ionogel, the ionogel being an ionic liquid immobilized by a matrix.

* * * * *